(12) United States Patent
Souza et al.

(10) Patent No.: US 11,814,356 B1
(45) Date of Patent: Nov. 14, 2023

(54) SALT OF CABOZANTINIB

(71) Applicant: Apotex Inc., Toronto (CA)

(72) Inventors: Fabio E. S. Souza, Brantford (CA); Alexander J. Stirk, Brantford (CA); Avedis Karadeolian, Brantford (CA); Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 18/127,726

(22) Filed: Mar. 29, 2023

(51) Int. Cl.
C07D 215/233 (2006.01)

(52) U.S. Cl.
CPC ...... C07D 215/233 (2013.01); C07B 2200/13 (2013.01)

(58) Field of Classification Search
CPC .......... C07D 215/233; C07B 2200/13
See application file for complete search history.

(56) References Cited

U.S. PATENT DOCUMENTS

| 2017/0044106 A1* | 2/2017 | Aftab ................. C07D 215/233 |
| 2021/0332014 A1 | 10/2021 | Chen et al. |

FOREIGN PATENT DOCUMENTS

| CN | 104649969 A | 5/2015 |
| CN | 105503717 A | 4/2016 |
| CN | 104109124 B | 8/2016 |
| CN | 104109128 B | 10/2016 |
| CN | 104961681 B | 6/2017 |
| CN | 104961680 B | 9/2017 |
| CN | 108341773 A | 7/2018 |
| IN | 00343563 A1 | 8/2020 |
| WO | 2010083414 A1 | 7/2010 |
| WO | 2015123639 A1 | 8/2015 |
| WO | 2015177758 A1 | 11/2015 |
| WO | 2016150963 A1 | 9/2016 |
| WO | 2016150966 A1 | 9/2016 |
| WO | 2018104954 A1 | 6/2018 |
| WO | 2018218233 A1 | 11/2018 |
| WO | 2019241504 A1 | 12/2019 |
| WO | 2020075196 A1 | 4/2020 |

OTHER PUBLICATIONS

Committee for Medicinal Products for Human Use, "Assment report for Cometriq (EMEA/H/C/002640/0000)", European Medicines Agency, 2014, 107 pages.
Rudnic et al., "Oral Solid Dosage Forms", Remington the Science and Practice of Pharmacy 21st Edition, 2006, Chapter 45, Lippincott Williams & Wilkins, Philadelphia.
Porter "Coating of Pharmaceutical Dosage Forms", Remington the Science and Practice of Pharmacy 21st Edition, 2006, Chapter 46, Lippincott Williams & Wilkins, Philadelphia.

* cited by examiner

Primary Examiner — Timothy R Rozof
(74) Attorney, Agent, or Firm — THE WEBB LAW FIRM

(57) ABSTRACT

Provided is a cabozantinib acesulfamate salt and a crystalline form thereof. Also provided are pharmaceutical compositions including the salt and crystalline form thereof, and methods of treatment of progressive, metastatic medullary thyroid cancer (MTC) or advanced renal cell carcinoma (RCC) that has been treated previously with anti-angiogenic therapy using the cabozantinib acesulfamate salt.

16 Claims, 2 Drawing Sheets

SALT OF CABOZANTINIB

BACKGROUND OF THE INVENTION

Field of the Invention

The present invention is directed to a novel salt of cabozantinib, a crystalline form thereof, pharmaceutical compositions containing this salt, and its use for the treatment cancer.

Description of Related Art

Cabozantinib (1), or N-(4-(6,7-dimethoxyquinolin-4-yloxy)phenyl)-N'-(4-fluorophenyl)cyclopropane-1,1-dicarboxamide is the active pharmaceutical ingredient (API) provided in the form of its (S)-malate salt (1:1) in branded prescription pharmaceuticals COMETRIQ® and CABOMETYX®. COMETRIQ® is indicated for use in the treatment of patients with progressive, metastatic medullary thyroid cancer (MTC) and CABOMETYX® is indicated for use in the treatment of patients with advanced renal cell carcinoma (RCC) who have received prior anti-angiogenic therapy.

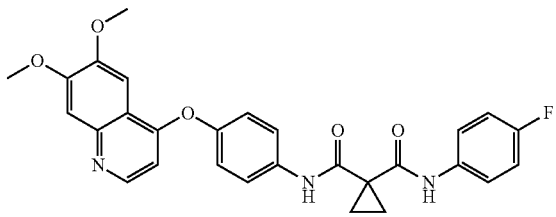

(1)

Cabozantinib salts and crystalline forms thereof are reported in, for example, WO 2010/083414 A1, CN 104109124 B, CN 104109128 B, CN 104649969 B, CN 104961680 B, CN 104961681 B, WO 2015/123639 A1, IN 1967/CHE/2014, WO 2015/177758 A1, CN 105503717 A, WO 2016/150963 A1, WO 2016/150966 A1, WO 2018/104954 A1, CN 108341773 A, WO 2018/218233 A1, WO 2019/241504 A1, US 2021/332014 A1 and WO 2020/075196 A1.

According to the European CHMP Assessment Report for COMETRIQ® (EMEA/H/C/002640/0000), cabozantinib has pH-dependent aqueous solubility, with very low solubility observed at a pH>3 but high permeability, placing cabozantinib in Class II of the Biopharmaceutics Classification System (BCS). A limiting factor in controlling drug absorption and bioavailability of Class II drug substances can be adequate solubilization of the drug in the aqueous environment of the gastrointestinal tract. As such, improvement in aqueous solubility of the drug substance can be directly correlated with improved drug effectiveness.

The solubility of individual salt and crystalline forms of a drug substance in an aqueous environment is an important aspect of their relative bioavailability, since the manner in which the salt or crystalline form dissolves can correspond to the amount of the drug substance that is available to be absorbed into the body to provide the intended therapeutic effect. One measure of solubility is intrinsic dissolution rate (IDR), which is defined as the dissolution rate of a substance under constant surface area conditions. For low solubility substances, higher IDR values can correlate with higher bioavailability following administration. However, if the goal is to establish bioequivalence to an existing form of a drug under investigation, substances with similar IDR values to the known form are preferred. Alternatively, for the development of extended or sustained release products, forms exhibiting lower IDR values are often preferable since they can provide slower dissolution of the drug independent of the excipients used in the formulation.

Different salt and/or crystalline forms of the same compound may have different crystal packing, thermodynamic, spectroscopic, kinetic, surface, and mechanical properties. For example, different salts and/or crystalline forms may have different stability properties such that a particular form may be less sensitive to heat, relative humidity (RH) and/or light. Different salts and/or crystalline forms of a compound may be more susceptible to moisture uptake, resulting in a potential alteration of the chemical and/or physical stability. Different salts may exist in more than one crystalline form, which can cause complexity in ensuring the stability of a desired crystalline form in a drug product. Different salts and/or crystalline forms of a compound may have different dissolution rates, thereby providing different pharmacokinetic parameters, which allow for specific forms to be used in order to achieve specific pharmacokinetic targets.

For example, a particular salt and/or crystalline form may provide more favourable compressibility and/or density properties, thereby providing more desirable characteristics for formulation and/or product manufacturing. Differences in stability between salts and/or crystalline forms of a drug may result from changes in chemical reactivity, such as differential oxidation. The melting point of a particular salt and/or crystalline form, particularly a low melting point, can contribute to issues during processing, which impact on both flow and compressibility performance. Particular salts and/or crystalline forms may also have different solubilities in aqueous environments, with implications related to formulation options and pharmacokinetics.

Therefore, there exists a need for novel salts and crystalline forms of cabozantinib for use in providing improved drug products containing cabozantinib, and commercially amenable processes for their manufacture.

SUMMARY OF THE INVENTION

The present invention provides a salt comprising cabozantinib and acesulfame, referred to as cabozantinib acesulfamate, and a crystalline form thereof. Acesulfame, in the form of acesulfamate potassium, is used as a sweetener in the food industry and as an inactive ingredient in drug products. Accordingly, it is expected that acesulfame can safely be used in materials intended for use in the preparation of pharmaceutical compositions intended for administration to humans. Further, cabozantinib acesulfamate exhibits form stability at high temperature and high humidity.

In addition, the processes for the manufacture of cabozantinib acesulfamate salt and a crystalline form thereof of the present invention are efficient and industrially compatible.

Accordingly, in a first aspect of the present invention, there is provided an acesulfamate salt of cabozantinib. In a preferred embodiment of the first aspect, the molar ratio of cabozantinib to acesulfame in the salt is approximately 1:1. In a more preferred embodiment of the first aspect, the salt has a weight percentage of water from approximately 2.9 wt % to approximately 4.5 wt %, or from approximately 3.2 wt % to approximately 4.0 wt %.

In a second aspect of the present invention, there is provided a crystalline form of cabozantinib acesulfamate, characterized by a PXRD diffractogram comprising peaks, expressed in degrees 2θ (±0.2°), at 9.5°, 11.2°, and 19.7°. More preferably, the salt of the second aspect is characterized by a PXRD diffractogram further comprising at least three peaks in the PXRD diffractogram, expressed in degrees 2θ (±0.2°), selected from the group consisting of: 9.1°, 10.2°, 12.7°, 15.9°, 17.4°, and 18.1°. In a further preferred embodiment of the second aspect, the PXRD diffractogram further comprises peaks, expressed in degrees 2θ (±0.2°), at 9.1°, 10.2°, 12.7°, 15.9°, 17.4°, and 18.1°. Preferably, the salt of the second aspect of the invention provides a PXRD diffractogram comprising peaks in substantially the same positions (±0.2° 2θ) as those shown in FIG. 1. In another preferred embodiment of the first aspect, the crystalline form is characterized by a DSC thermogram comprising an endothermic peak with a peak onset at approximately 215° C. and a peak maximum at approximately 216° C. More preferably, the DSC thermogram is substantially the same in appearance as the DSC thermogram provided in FIG. 2. In a further preferred embodiment of the second aspect, the molar ratio of cabozantinib to acesulfame is approximately 1:1. In a more preferred embodiment of the second aspect, the form has a weight percentage of water from approximately 2.9 wt % to approximately 4.5 wt %, or from approximately 3.2 wt % to approximately 4.0 wt %.

In a third aspect of the present invention, there is provided a pharmaceutical composition comprising a cabozantinib acesulfamate salt according to the first or second aspects of the invention, and one or more pharmaceutically acceptable excipients. Preferably, the pharmaceutical composition is in the form of a capsule or a tablet. Preferably, the pharmaceutical composition of the third aspect comprises an amount of the cabozantinib acesulfamate of the first or second aspect that is equivalent to 20, 40, 60, or 80 mg of cabozantinib free base.

In a fourth aspect of the present invention, there is provided the use of a cabozantinib acesulfamate salt according to the first or second aspect of the invention, or a pharmaceutical composition of the third aspect of the invention, in the treatment of cancer. In a preferred embodiment of the fourth aspect, the cancer is thyroid cancer or renal cell carcinoma. More preferably, the cancer is progressive, metastatic medullary thyroid cancer (MTC) or advanced renal cell carcinoma (RCC) that has been treated previously with anti-angiogenic therapy.

Other aspects and features of the present invention will become apparent to those ordinarily skilled in the art upon review of the following description of specific embodiments of the invention in conjunction with the accompanying FIGS.

BRIEF DESCRIPTION OF THE DRAWINGS

Embodiments of the present invention are described, by way of example only, with reference to the attached drawings.

DESCRIPTION OF THE INVENTION

The present invention provides a cabozantinib acesulfamate salt and a crystalline form thereof. Acesulfame, in the form of its potassium salt, is used as a sweetener in the food industry and is also included in both the U.S. Food & Drug Administration's (FDA's) Substances Added to Food inventory (formerly Everything Added to Food in the United States (EAFUS)) list and the Inactive Ingredient Database (IID). The Substances Added to Food inventory contains approximately 4,000 substances, and includes information on food additives, colour additives, Generally Recognized As Safe (GRAS) substances, and prior-sanctioned substances. The IID list provides information on inactive ingredients present in FDA-approved drug products. Once an inactive ingredient has appeared in an approved drug product, the inactive ingredient is not considered new, and may require a less extensive review the next time it is included in a new drug product. In addition to pharmaceutical acceptability, the acesulfamate counterion may offer a dual purpose by imparting a sweet taste that could be exploited in certain pharmaceutical formulations such as oral solutions.

The present invention provides a cabozantinib acesulfamate salt and a crystalline form thereof providing improved properties over known salts of cabozantinib. Properties that differ between the invention and known forms of cabozantinib include one or more of the following: packing properties such as molar volume, density and hygroscopicity; thermodynamic properties such as melting point and solubility; kinetic properties such as dissolution rate and chemical/polymorphic stability; surface properties such as crystal habit; and/or mechanical properties such as hardness, tensile strength, cohesiveness, compactability, tableting, handling, flow, and blending.

Additionally, a process for the manufacture of cabozantinib acesulfamate and a crystalline form thereof of the present invention is efficient and industrially compatible, using a Class 3 solvent established by the ICH (International Council for Harmonization of Technical Requirements for Pharmaceuticals for Human Use) as having low toxicity.

Figure 1:
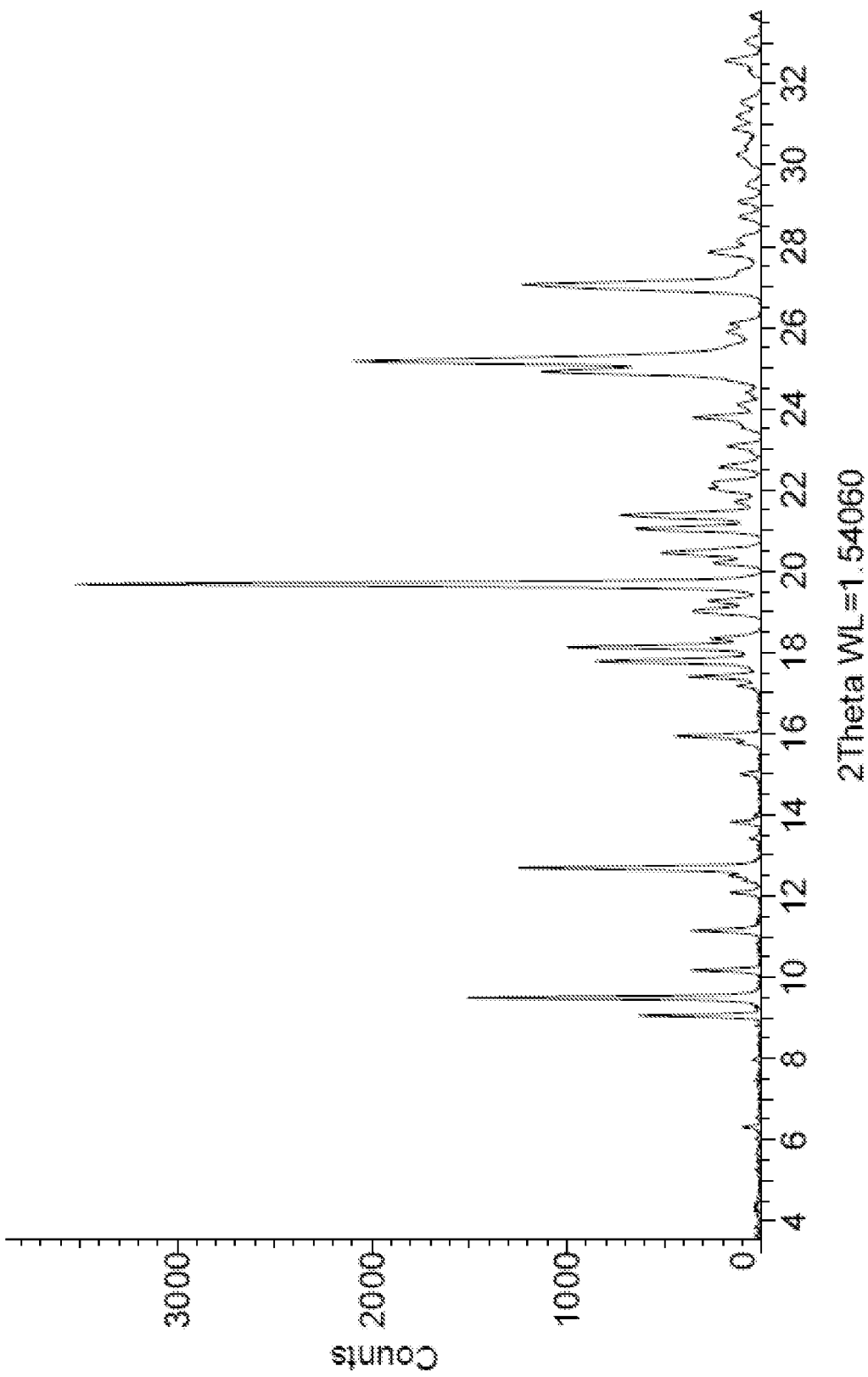
FIG. 1 is a representative PXRD diffractogram of cabozantinib acesulfamate Form APO-I as prepared in Example 1.

Depending on the manner in which a crystalline form of the present invention is prepared, and the methodology and instrument used for PXRD analysis, the intensity of a given peak observed in a PXRD diffractogram of the crystalline form may vary when compared to the same peak in the representative PXRD diffractogram provided in FIG. 1. Thus, differences in relative peak intensities between peaks in a PXRD diffractogram for a given crystalline form may be observed when compared to the relative peak intensities of the peaks in the representative PXRD diffractogram of FIG. 1. Any such differences may be due, in part, to the preferred orientation of the sample and its deviation from the ideal random sample orientation, the preparation of the sample for analysis, and the methodology applied for the analysis. Such variations are known and understood by a person of skill in the art, and any such variations do not depart from the invention disclosed herein.

In addition to the differences in relative peak intensities that may be observed in comparison to the representative PXRD diffractogram provided in FIG. 1, it is understood that individual peak positions may vary between ±0.2° 2θ from the values observed in the representative PXRD diffractograms provided in FIG. 1 for a crystalline form of the invention, or listed in Table 1. Such variations are known and understood by a person of skill in the art, and any such variations do not depart from the invention disclosed herein.

Further, depending on the instrument used for X-ray analysis and its calibration, uniform offsets in the peak position of each peak in a PXRD diffractogram of greater that 0.2° 2θ may be observed when compared to the representative PXRD diffractogram provided in FIG. 1. Thus, the PXRD diffractogram of a crystalline form of the present invention may, in some circumstances, display the same relative peak positions as observed in the representative PXRD diffractograms provided in FIG. 1, with the exception that each peak is offset in the same direction, and by approximately the same amount, such that the overall PXRD diffractogram is substantially the same in appearance as the PXRD diffractogram of FIG. 1, with the exception of the uniform offset in peak positions. The observation of any such uniform peak shift in a PXRD diffractogram does not depart from the invention disclosed herein given that the relative peak positions of the individual peaks within the PXRD diffractogram remain consistent with the relative peak positions observed in the PXRD diffractogram of FIG. 1.

Figure 2:
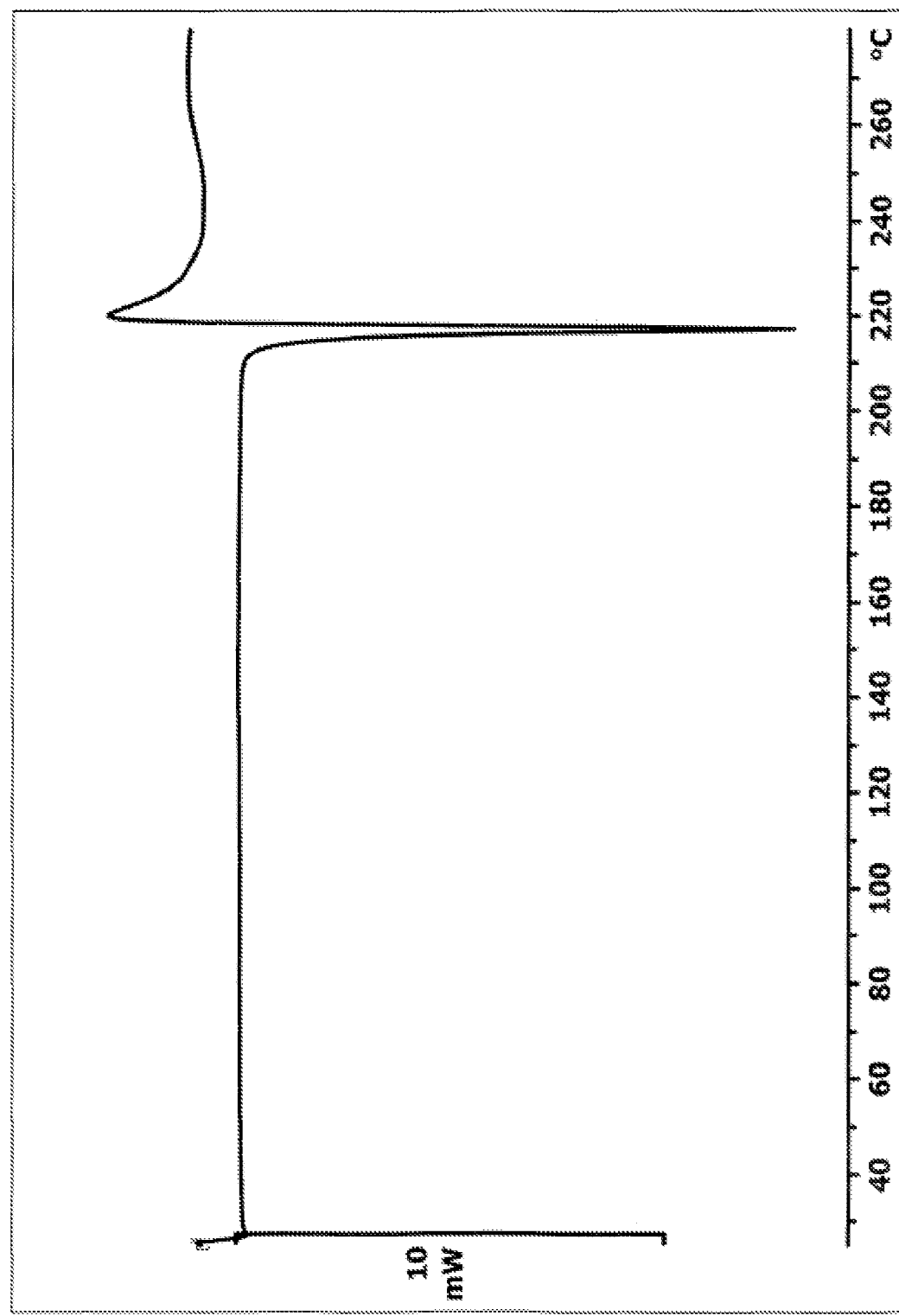
FIG. 2 is a representative DSC thermogram of cabozantinib acesulfamate Form APO-I as prepared in Example 1.

Depending on the manner in which a crystalline form is prepared, the methodology and instrument used for DSC analysis, it is understood that peaks corresponding with thermal events in a DSC thermogram may vary between ±2° C. from the values observed in the representative DSC thermogram provided in FIG. 2 and described herein. Such variations are known and understood by a person of skill in the art, and any such variations do not depart from the invention disclosed herein.

As used herein, the term 'crystalline form' refers to a cabozantinib salt of fixed composition with a particular arrangement of components in its crystal lattice, and which may be identified by physical characterization methods such as PXRD. As used herein, the term crystalline form is intended to include single-component and multiple-component crystalline forms of a cabozantinib salt. Single-component forms of a cabozantinib salt, such as those in the prior art, consist solely of cabozantinib and the counterion in the repeating unit of the crystal lattice. Multiple-component forms of a cabozantinib salt include solvates (and hydrates) of a cabozantinib salt wherein a solvent (or water) is also incorporated into the crystal lattice.

As used herein, the term "room temperature" refers to a temperature in the range of 20° C. to 25° C.

Unless defined otherwise herein, the term "approximately", when used in reference to molar ratios, allows for a variance of plus or minus 10%, or plus or minus 5%, or plus or minus 1% of the stated value. It should be understood that any numerical range recited herein is intended to include all sub-ranges subsumed therein.

When describing the embodiments of the present invention there may be a common variance to a given temperature or time that would be understood or expected by the person skilled in the art to provide substantially the same result. For example, when reference is made to a particular temperature, it is to be understood by the person skilled in the art that there is an allowable variance of ±5° C. associated with that temperature. When reference is made to a particular time, it is to be understood that there is an allowable variance of ±10 minutes when the time is one or two hours, and ±1 hour when longer periods of time are referenced.

In one embodiment of the present invention, there is provided a new salt of cabozantinib, cabozantinib acesulfamate Form APO-I, wherein the molar ratio of cabozantinib to acesulfame is approximately 1:1.

Cabozantinib acesulfamate Form APO-I can be characterized by a PXRD diffractogram comprising, among other peaks, characteristic peaks, expressed in degrees 2θ (±0.2°), at 9.5°, 11.2° and 19.7°. Preferably, the PXRD diffractogram further comprises at least three peaks, expressed in degrees 2θ (±0.2°), selected from the group consisting of 9.1°, 10.2°, 12.7°, 15.9°, 17.4°, and 18.1°. More preferably, the PXRD diffractogram further comprises peaks, expressed in degrees 2θ (±0.2°), at 9.1°, 10.2°, 12.7°, 15.9°, 17.4°, and 18.1°. PXRD studies of uncapped samples of cabozantinib acesulfamate Form APO-I maintained in a 40° C./75% RH (relative humidity) stability chamber for at least 4 weeks showed that no change in the crystalline form occurred.

An illustrative PXRD diffractogram of cabozantinib acesulfamate Form APO-I, as prepared in Example 1, is shown in FIG. 1. A peak listing, comprising representative peaks from the PXRD diffractogram in FIG. 1, and their relative intensities, is provided in Table 1. Although illustrative of the PXRD diffractogram that is provided for the cabozantinib acesulfamate Form APO-I of the present invention, the relative intensities of the peaks are variable. Thus, depending on a particular sample, the prominence or relative intensity of the peaks observed may differ from those in the illustrative PXRD diffractogram and peak listing.

TABLE 1

Relative peak intensities of cabozantinib acesulfamate Form APO-I from FIG. 1

| Angle (2θ) | Relative intensity (%) |
|---|---|
| 6.32 | 2.8 |
| 9.06 | 17.9 |
| 9.50 | 42.7 |
| 10.18 | 10.2 |
| 11.15 | 10.2 |
| 12.70 | 35.2 |
| 15.94 | 12.6 |
| 17.41 | 10.7 |
| 17.78 | 24.2 |
| 18.13 | 28.3 |
| 19.02 | 10.1 |
| 19.68 | 100.0 |
| 20.45 | 14.5 |
| 21.05 | 18.3 |
| 21.38 | 20.5 |
| 25.17 | 59.5 |

An illustrative DSC thermogram of cabozantinib acesulfamate Form APO-I is shown in FIG. 2. The DSC thermogram may be further characterized by an endothermic peak with a peak onset at approximately 215° C. and a peak maximum at approximately 216° C.

As described in Example 1, cabozantinib acesulfamate Form APO-I can be prepared by combining approximately equimolar amounts of cabozantinib free base with acesulfame in a mixture of water and a suitable water-miscible solvent, preferably acetone, and maintaining the mixture at a suitable temperature, preferably room temperature, for a suitable time, preferably between 12 and 20 hours. The resulting suspension is isolated and dried, if necessary, preferably in vacuo and at room temperature.

In a further embodiment of the invention, there is provided a pharmaceutical composition comprising cabozantinib acesulfamate, with one or more pharmaceutically acceptable excipients. Preferably, the pharmaceutical composition comprises cabozantinib acesulfamate Form APO-I. Preferably, the pharmaceutical composition is a solid dosage form suitable for oral administration, such as a capsule, tablet, pill, powder, or granulate. Most preferably, the pharmaceutical composition is a tablet or a capsule. Preferably, the pharmaceutical composition provides a dose of cabozantinib acesulfamate that is equivalent to the 20 mg, 40 mg, or 60 mg of cabozantinib free base found in CABOMETYX® drug products or the 20 mg or 80 mg of cabozantinib free base found in COMETRIQ® drug products.

Suitable pharmaceutically acceptable excipients are preferably inert with respect to the cabozantinib salts of the present invention and may include, for example, one or more excipients selected from binders such as lactose, starches, modified starches, sugars, gum acacia, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone, gelatine, polyvinylpyrrolidone (PVP), and sodium alginate; fillers or diluents such as lactose, sugar, starches, modified starches, mannitol, sorbitol, inorganic salts, cellulose derivatives (e.g., microcrystalline cellulose, cellulose), calcium sulphate, xylitol, and lactitol; disintegrants such as croscarmellose sodium, crospovidone, polyvinylpyrrolidone, sodium starch glycollate, corn starch, microcrystalline cellulose, hydroxypropyl methylcellulose, and hydroxypropyl cellulose; lubricants such as magnesium stearate, magnesium lauryl stearate, sodium stearyl fumarate, stearic acid, calcium stearate, zinc stearate, potassium benzoate, sodium benzoate, myristic acid, palmitic acid, mineral oil, hydrogenated castor oil, medium-chain triglycerides, poloxamer, polyethylene glycol, and talc; and dispersants or solubility enhancing agents, such as cyclodextrins, glyceryl monostearate, hypromellose, meglumine, Poloxamer, polyoxyethylene castor oil derivatives, polyoxyethylene stearates, polyoxylglycerides, povidone, and stearic acid. Other excipients including preservatives, stabilisers, anti-oxidants, silica flow conditioners, anti-adherents, or glidants may be added as required. Other suitable excipients and the preparation of solid oral dosage forms are well known to a person of skill in the art, and is described generally, for example, in *Remington The Science and Practice of Pharmacy 21st Edition* (Lippincott Williams & Wilkins: Philadelphia; 2006; Chapter 45).

Optionally, when the pharmaceutical compositions are solid dosage forms, the solid dosage forms may be prepared with coatings, such as enteric coatings and extended-release coatings, using standard pharmaceutical coatings. Such coatings, and their application, are well known to persons skilled in the art, and are described, for example, in *Remington The Science and Practice of Pharmacy 21st Edition* (Lippincott Williams & Wilkins: Philadelphia; 2006; Chapter 46).

Also provided herein are methods for treating cancer, for example progressive, metastatic medullary thyroid cancer (MTC) or advanced renal cell carcinoma (RCC) that has been treated previously with anti-angiogenic therapy(s), comprising administering the salt(s) of cabozantinib disclosed herein, or a pharmaceutical composition comprising the salt(s) of cabozantinib disclosed herein, to a human subject in a therapeutically effective amount for the treatment of cancer. As used herein, the phrase "therapeutically effective amount" means that amount of cabozantinib, or a pharmaceutically acceptable salt thereof, that will elicit a biological or medical response of a tissue, system, or patient that is being sought by the administrator (such as a researcher, doctor, or veterinarian) which includes alleviation of the symptoms of the condition or disease being treated and the prevention, slowing, or halting of progression of the condition or disease, including but not limited to cancer, for example a dose of cabozantinib acesulfamate that is equivalent to the 20 mg, 40 mg, or 60 mg of cabozantinib free base found in CABOMETYX® drug products or the 20 mg or 80 mg of cabozantinib free base found in COMETRIQ® drug products.

Examples

The following non-limiting examples are illustrative of some of the aspects and embodiments of the invention described herein.

The PXRD of cabozantinib free base used as a starting material in the following example was consistent with Form III disclosed in WO 2015/123639 A1. Acesulfame used as starting material in the following example was obtained by stirring an ethyl acetate suspension of acesulfame potassium and a stoichiometric amount of 85% phosphoric acid for about 3 hours, filtering the organic layer and concentrating the solution to dryness.

PXRD Analysis:

PXRD diffractograms were recorded on a Bruker D8 Discover powder X-ray diffractometer (Bruker AXS LLC, Karlsruhe, Germany). The sample holder was oscillated along x and y axes during the measurement. The generator was a Incoatec Microfocus Source (IμS) Cu tube ($\lambda$=1.54060 Å) with a voltage of 50 kV and current of 1.00 mA, using a divergence slit of 0.1 mm and collimator of 2.0 mm. For each sample, one frame was collected using a still scan with a PILATUS3 R 100K-A detector at the distance of 294.2 mm from the sample. Raw data were evaluated using the program DIFFRAC.EVA (Bruker AXS LLC, Karlsruhe, Germany).

Differential Scanning Calorimetry Analysis:

The DSC thermogram was collected on a Mettler-Toledo 821e instrument. The sample (1.66 mg) was weighed into a 40 μL aluminum pan and were crimped closed with an aluminum lid having a 50 μm pinhole. The sample was analyzed under a flow of nitrogen (50±5 mL/min) at a scan rate of 10° C./minute between 25° C. and 280° C.

Example 1: Preparation of Cabozantinib Acesulfamate Form APO-I

To a suspension of cabozantinib free base (268 mg) in acetone (3.5 mL) was added water (1.5 mL) and acesulfame (101 mg), and the resulting suspension was stirred at ambient temperature for 16 hours. The solids were collected by vacuum filtration, washed with acetone (2×0.7 mL), and dried in vacuo at room temperature for approximately 24 hours. Cabozantinib acesulfamate Form APO-I was obtained as a white solid (229 mg). $^1$H NMR analysis of the solid (DMSO-$d_6$) revealed a molar ratio of cabozantinib:acesulfame of approximately 1:1. The PXRD diffractogram and DSC thermogram of a sample prepared by this method are shown in FIG. 1 and FIG. 2, respectively. TGA (25-360° C.@10° C./min; 85 mL/min N$_2$ flow) of the sample showed a weight loss of approximately 3.6% between 200° C. and 240° C., which may be consistent with a 1.5 hydrate (sesquihydrate).

$^1$H NMR (300 MHz, DMSO-$d_6$): 10.30 (s, 1H), 10.01 (s, 1H), 8.76 (d, J=6.4 Hz, 1H), 7.84 (d, J=9.0 Hz, 2H), 7.71 (s, 1H), 7.64 (dd, J=5.2, 9.0 Hz, 2H), 7.50 (s, 1H), 7.35 (d, J=9.0 Hz, 2H), 7.16 (t, J=8.9 Hz, 2H), 6.77 (d, J=6.3 Hz, 1H), 5.40 (s, 1H), 4.04 (s, 3H), 4.02 (s, 3H), 1.94 (d, J=0.8 Hz, 3H), 1.49 (m, 4H).

The invention claimed is:

1. A crystalline form of cabozantinib acesulfamate, characterized by a PXRD diffractogram comprising peaks, expressed in degrees 2θ (±0.2°), at 9.5°, 11.2°, and 19.7°.

2. The crystalline form of claim 1, further comprising at least three peaks in the PXRD diffractogram, expressed in degrees 2θ (±0.2°), selected from the group consisting of: 9.1°, 10.2°, 12.7°, 15.9°, 17.4°, and 18.1°.

3. The crystalline form of claim 1, further comprising peaks in the PXRD diffractogram, expressed in degrees 2θ (±0.2°), at 9.1°, 10.2°, 12.7°, 15.9°, 17.4°, and 18.1°.

4. The crystalline form of claim 2, characterized by a DSC thermogram comprising an endothermic peak with a peak onset of approximately 215° C. and a peak maximum of approximately 216° C.

5. The crystalline form of claim 2, characterized by a DSC thermogram that is substantially the same in appearance as the DSC thermogram provided in FIG. 2.

6. The crystalline form of claim 1, providing a PXRD diffractogram comprising peaks in substantially the same positions (±0.2° 2θ) as those shown in FIG. 1.

7. The crystalline form of claim 1, wherein the molar ratio of cabozantinib to acesulfame is approximately 1:1.

8. The crystalline form of claim 7, having a weight percentage of water from approximately 2.9 wt % to approximately 4.5 wt %.

9. The crystalline form of claim 7, having a weight percentage of water from approximately 3.2 wt % to approximately 4.0 wt %.

10. A pharmaceutical composition comprising the crystalline form of cabozantinib acesulfamate according to claim 1, and one or more pharmaceutically acceptable excipients.

11. The pharmaceutical composition of claim 10, wherein the pharmaceutical composition is a capsule or a tablet.

12. The pharmaceutical composition of claim 11, wherein the pharmaceutical composition is a capsule.

13. The pharmaceutical composition of claim 11, wherein the pharmaceutical composition is a tablet.

14. A method for treating cancer, comprising administering the crystalline form of cabozantinib acesulfamate according to claim 1 to a human subject in a therapeutically effective amount for the treatment of cancer.

15. The method of claim 14, wherein the cancer is progressive, metastatic medullary thyroid cancer (MTC) or advanced renal cell carcinoma (RCC) that has been treated previously with anti-angiogenic therapy.

16. A method for treating cancer, comprising administering the pharmaceutical composition of claim 11 to a human subject in a therapeutically effective amount for the treatment of cancer.

\* \* \* \* \*